(12) United States Patent
Suzuki et al.

(10) Patent No.: US 8,198,592 B2
(45) Date of Patent: Jun. 12, 2012

(54) MEASURING INSTRUMENT AND MEASURING METHOD

(75) Inventors: Yoshimasa Suzuki, Tokyo (JP); Mitsuru Namiki, Tokyo (JP)

(73) Assignee: Olympus Corporation, Tokyo (JP)

( * ) Notice: Subject to any disclaimer, the term of this patent is extended or adjusted under 35 U.S.C. 154(b) by 808 days.

(21) Appl. No.: 12/360,178

(22) Filed: Jan. 27, 2009

(65) Prior Publication Data
US 2009/0189080 A1 Jul. 30, 2009

(30) Foreign Application Priority Data

Jan. 28, 2008 (JP) ................................ 2008-016528

(51) Int. Cl.
*G01N 21/64* (2006.01)
(52) U.S. Cl. ............ 250/363.01; 250/458.1; 250/459.1; 250/361 R; 356/432
(58) Field of Classification Search .............. 250/363.01
See application file for complete search history.

(56) References Cited

U.S. PATENT DOCUMENTS

| | | | | |
|---|---|---|---|---|
| 5,034,613 A | * | 7/1991 | Denk et al. ................. | 250/458.1 |
| 5,062,942 A | * | 11/1991 | Kambara et al. ............. | 204/612 |
| 6,169,289 B1 | * | 1/2001 | White et al. ................ | 250/458.1 |
| 7,439,522 B2 | * | 10/2008 | Shirai et al. ................ | 250/458.1 |
| 2006/0197034 A1 | * | 9/2006 | Shirai et al. ................ | 250/458.1 |
| 2007/0008536 A1 | * | 1/2007 | Mitani et al. ................... | 356/417 |
| 2009/0236543 A1 | * | 9/2009 | Ooki et al. ................. | 250/459.1 |

FOREIGN PATENT DOCUMENTS

JP 2007-078574 3/2007

* cited by examiner

*Primary Examiner* — David Porta
*Assistant Examiner* — Djura Malevic
(74) *Attorney, Agent, or Firm* — Pillsbury Winthrop Shaw Pittman, LLP

(57) ABSTRACT

A measuring instrument has a light source for irradiating light including rays of light having the wavelength of excitation light, an objective lens for focusing light irradiated from the light source to a predetermined focusing position, a first mirror for directly reflecting light from the objective lens, a second mirror for reflecting light reflected by the first mirror, the second mirror having an aperture P, and a measuring device for measuring light generated from a sample and having a wavelength different from the wavelength of excitation light, and the sample being arranged between the first mirror and the second mirror, the focusing position of the objective lens being made to agree with the position of the aperture P, and the measuring device being adapted to measure light of a wavelength different from the wavelength of excitation light generated from the sample and passing through the aperture P.

20 Claims, 12 Drawing Sheets

1st instance: $(2-\sqrt{2})L \leq f \leq L$

2nd instance: $f=(2-\sqrt{2})L$

3rd instance: $L/2 < f < (2-\sqrt{2})L$

4th instance: $L/2 = f$

<u>5th instance: 0≤f≤L/2</u>

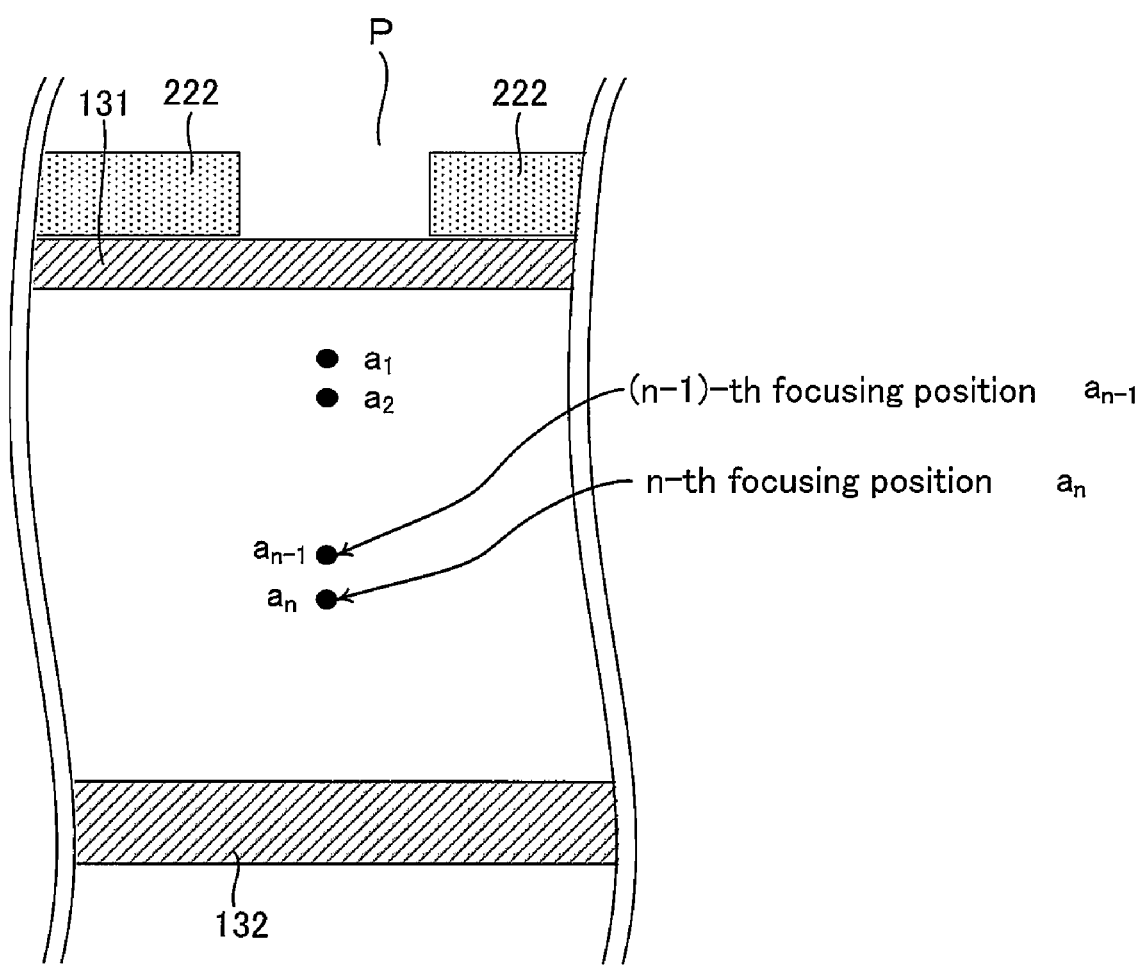

FIG.9A

| position | material (medium) | gap between materials (mediums) | refractive index | air-equivalent length |
|---|---|---|---|---|
| 1st substrate | PS (polystyrene) | L1=0.5mm | n1=1.59 | L1/n1=0.314mm |
| space (R) | sample aqueous solution | L2=1.0mm | n2=1.33 | L2/n2=0.752mm |
| 2nd substrate | PS (polystyrene) | L3=1.0mm | n3=1.59 | L3/n3=0.629mm |
| 2nd substrate to 1st mirror | air | L4=1.0mm | n4=1 | L4/n4=1mm |
| | | | | L=2.695mm |

FIG.9B

| focal length of 1st mirror | f=1.213 (=0.45×L) |
|---|---|

FIG.9C

| 1st focusing position | $a_1$ | 2.205mm |
|---|---|---|
| 2nd focusing position | $a_2$ | 1.959mm |
| 3rd focusing position | $a_3$ | 1.876mm |
| 4th focusing position | $a_4$ | 1.852mm |
| 5th focusing position | $a_5$ | 1.845mm |
| 6th focusing position | $a_6$ | 1.844mm |
| 7th focusing position | $a_7$ | 1.843mm |
| 8th focusing position | $a_8$ | 1.843mm |
| ⋮ | ⋮ | ⋮ |
| ∞-th focusing position | $a_\infty$ | 1.843mm |

MEASURING INSTRUMENT AND MEASURING METHOD

REFERENCE TO RELATED APPLICATION

This application is based upon and claims the benefit of priority from the prior Japanese Patent Application No. 2008-16528, filed on Jan. 28, 2008, the entire contents of which including the specification, the drawings and the abstract are incorporated herein by reference.

BACKGROUND OF THE INVENTION

1. Field of the Invention

The present invention relates to a fluorescence measuring instrument for micro samples. More particularly, the present invention relates to a measuring instrument and a measuring method for measuring a micro fluorescent spot on a sample such as a microchip.

2. Description of the Related Art

LOC (Lab-on-a-chip) technologies have been and are being studied and developed for the purpose of downsizing known measuring instruments and allowing a very small quantity of a liquid reagent to react with a sample. For preparing a LOC, a groove is formed on the surface of a chip made of plastic, glass or silicon and having a surface of several to ten centimeters square or less so as to make a quantity of the sample such as a blood minute. Then, a reagent solution or a sample is made to flow in the groove for isolation and reaction in order to analyze a very small quantity of the sample. Such a technique provides advantages including that it can reduce the quantity of sample, the quantity of reagent and the quantity of wastes including the consumables used for detection and waste liquid as well as the time required for detection.

Measuring instruments to be used with LOC technologies include those that are designed to detect fluorescence from a very small quantity of a sample by irradiating a substrate (micro array) with excitation light.

SUMMARY OF THE INVENTION

In an aspect of the present invention, there is provided a measuring instrument including: a light source for irradiating excitation light; an objective lens; a first mirror; a second mirror; and a measuring device, and the second mirror being arranged between the objective lens and the first mirror with the mirror surface of the first mirror facing the mirror surface of the second mirror; the first mirror having a curved surface with the center of curvature thereof disposed on the optical axis of the objective lens at the side of the second mirror; and the second mirror having an aperture at a position on the optical axis, the position of the aperture agreeing with the focal length of the objective lens.

In another aspect of the present invention, there is provided a measuring instrument including: a light source for irradiating light including rays of light having the wavelength of excitation light; an objective lens for focusing light irradiated from the light source to a predetermined focusing position; a first mirror for reflecting light from the objective lens; a second mirror for reflecting light reflected by the first mirror, the second mirror having an aperture; and a measuring device for measuring light generated from a sample and having a wavelength different from the wavelength of excitation light, and the sample being arranged between the first mirror and the second mirror; the focusing position of the objective lens being made to agree with the position of the aperture; the measuring device being adapted to measure light of a wavelength different from the wavelength of excitation light generated from the sample and passing through the aperture.

In still another aspect of the present invention, there is provided a measuring instrument including: a light source for irradiating light including rays of light having the wavelength of excitation light; an objective lens for focusing light irradiated from the light source to a predetermined focusing position; a first mirror for reflecting light from the objective lens; a second mirror for reflecting light reflected by the first mirror, the second mirror having an aperture; a focusing lens for focusing light generated from a sample and having a wavelength different from the wavelength of excitation light; a measuring device for measuring light generated from a sample and having a wavelength different from the wavelength of excitation light; and an excitation light cut filter arranged immediately in front of the measuring device at the light receiving side thereof to cut excitation light, and the sample being arranged between the first mirror and the second mirror; the focusing position of the objective lens being made to agree with the position of the aperture so as to make the focusing position of excitation light and the measuring device show a conjugate positional relationship; and the measuring device being adapted to measure light of a wavelength different from the wavelength of excitation light generated from the sample.

Preferably, in the measuring instrument according to the present invention, the second mirror is a dichroic mirror.

Preferably, in the measuring instrument according to the present invention, $f<L$ where the air-equivalent length between the first mirror and the second mirror is L and the focal length of the first mirror is f.

Preferably, in the measuring instrument according to the present invention, $f<L/2$ where the air-equivalent length between the first mirror and the second mirror is L and the focal length of the first mirror is f.

Preferably, in the measuring instrument according to the present invention, the reflection surface of the second mirror is a curved surface.

In still another aspect of the present invention, there is provided a measuring method including: arranging a measuring device having: a light source for irradiating excitation light; an objective lens; a first mirror; a second mirror; and a measuring device, and the second mirror being arranged between the objective lens and the first mirror with the mirror surface of the first mirror facing the mirror surface of the second mirror; the first mirror having a curved surface with the center of curvature thereof disposed on the optical axis of the objective lens at the side of the second mirror; and the second mirror having an aperture at a position on the optical axis, the position of the aperture agreeing with the focal length of the objective lens, and arranging a sample separated from the point of intersection of the optical axis and the first mirror by a distance of $Lf/(L-f)$ at the side of the second mirror relative to the point of intersection on the optical axis to measure light emitted from the sample;

where L being the air-equivalent length between the first mirror and the second mirror; and f being the focal length of the first mirror.

In still another aspect of the present invention, there is provided a measuring method including: arranging a measuring device having: a light source for irradiating excitation light; an objective lens; a first mirror; a second mirror; and a measuring device, and the second mirror being arranged between the objective lens and the first mirror with the mirror surface of the first mirror facing the mirror surface of the second mirror; the first mirror having a curved surface with the center of curvature thereof disposed on the optical axis of the objective lens at the side of the second mirror; the second mirror having an aperture at a position on the optical axis, the position of the aperture agreeing with the focal length of the objective lens, and arranging a sample separated from the point of intersection of the optical axis and the first mirror by a distance of $Lf/(L-f)$ at the side of the second mirror relative to the point of intersection on the optical axis to measure light emitted from the sample; and arranging a sample at all X positions located at the side of the second mirror relative to the point of intersection of the optical axis and the first mirror on the optical axis and satisfying the requirement as defined below;

$$L-(L^2-2fL)^{1/2} \leq X \leq Lf/(L-f);$$

where X being the distance from the point of intersection, L being the air-equivalent length between the first mirror and the second mirror;

f being the focal length of the first mirror.

In still another aspect of the present invention, there is provided a measuring method including: arranging a measuring device having: a light source for irradiating excitation light; an objective lens; a first mirror; a second mirror; and a measuring device; the second mirror being arranged between the objective lens and the first mirror with the mirror surface of the first mirror facing the mirror surface of the second mirror; the first mirror having a curved surface with the center of curvature thereof disposed on the optical axis of the objective lens at the side of the second mirror; the second mirror having an aperture at a position on the optical axis, the position of the aperture agreeing with the focal length of the objective lens; and operating adjustment of the instrument when observing light generated in a sample of a wavelength different from the wavelength of excitation light by means of the measuring device and showing a level of luminance exceeding the measurable limit of the measuring device.

In still another aspect of the present invention, there is provided a measuring method including: arranging a measuring device having: a light source for irradiating light including rays of light having the wavelength of excitation light; an objective lens for focusing light irradiated from the light source to a predetermined focusing position; a first mirror for reflecting light from the objective lens; a second mirror for reflecting light reflected by the first mirror, the second mirror having an aperture; and a measuring device for measuring light generated from a sample and having a wavelength different from the wavelength of excitation light; the sample being arranged between the first mirror and the second mirror; the focusing position of the objective lens being made to agree with the position of the aperture; the measuring device being adapted to measure light of a wavelength different from the wavelength of excitation light generated from the sample and passing through the aperture; and operating adjustment of the instrument when observing light generated in a sample of a wavelength different from the wavelength of excitation light by means of the measuring device and showing a level of luminance exceeding the measurable limit of the measuring device.

In still another aspect of the present invention, there is provided a measuring method including: arranging a measuring device having: a light source for irradiating light including rays of light having the wavelength of excitation light; an objective lens for focusing light irradiated from the light source to a predetermined focusing position; a first mirror for reflecting light from the objective lens; a second mirror for reflecting light reflected by the first mirror, the second mirror having an aperture; a focusing lens for focusing light generated from a sample and having a wavelength different from the wavelength of excitation light; a measuring device for measuring light generated from a sample and having a wavelength different from the wavelength of excitation light; and an excitation light cut filter arranged immediately in front of the measuring device at the light receiving side thereof to cut excitation light; the sample being arranged between the first mirror and the second mirror; the focusing position of the objective lens being made to agree with the position of the aperture so as to make the focusing position of excitation light and the measuring device show a conjugate positional relationship; the measuring device being adapted to measure light of a wavelength different from the wavelength of excitation light generated from the sample; and operating adjustment of the instrument when observing light generated in a sample of a wavelength different from the wavelength of excitation light by means of the measuring device and showing a level of luminance exceeding the measurable limit of the measuring device.

Preferably, in a measuring method according to the present invention, the adjustment of the measuring device is arranging an ND filter on the measuring optical path, lowering the output of the light source if the output of the light source is variable, lowering the gain of the measuring device or reducing the exposure time of the measuring device.

In still another aspect of the present invention, there is provided a measuring method including: arranging a first mirror; arranging a microchip containing a sample on the first mirror; arranging a second mirror for reflecting light reflected by the first mirror, the second mirror having an aperture; causing excitation light from a light source for irradiating excitation light to be focused to the aperture by means of an objective lens and enter the microchip; and measuring light radiated from the sample contained in the microchip and having a wavelength different from the wavelength of excitation light.

Preferably, in a measuring method according to the present invention, $f<L$ where the air-equivalent length between the first mirror and the second mirror is L and the focal length of the first mirror is f.

Preferably, in a measuring method according to the present invention, $f<L/2$ where the air-equivalent length between the first mirror and the second mirror is L and the focal length of the first mirror is f.

Preferably, in a measuring method according to the present invention, the microchip is formed by: a first substrate having a thickness of L1 and a refractive index of n1; a second substrate having a thickness of L3 and a refractive index of n3; and distance between the first substrate and the second substrate being L2, and a space containing a sample having a refractive index of n2, and the distance between the first mirror and the second substrate being L4, the space being filled with a medium having a refractive index of n4, the focal length of the first mirror being f; and $$L3/n3+L4/n4 < Lf/(L-f) < L2/n2+L3/n3+L4/n4;$$

the air-equivalent length L being defined to be $$L=L1/n1+L2/n2+L3/n3+L4/n4.$$

Preferably, in a measuring method according to the present invention, the microchip is formed by: a first substrate having a thickness of L1 and a refractive index of n1; a second substrate having a thickness of L3 and a refractive index of n3; and distance between the first substrate and the second substrate being L2, and a space containing a sample having a refractive index of n2, and the distance between the first mirror and the second substrate being L4, the space being filled with a medium having a refractive index of n4, the focal length of the first mirror being f; and $$L3/n3+L4/n4 < L-(L^2-2fL)^{1/2} < L2/n2+L3/n3+L4/n4;$$

the air-equivalent length L being defined to be $$L=L1/n1+L2/n2+L3/n3+L4/n4.$$

BRIEF DESCRIPTION OF THE DRAWINGS

FIG. 5A is a schematic illustration of convergence of focusing positions of the embodiment of measuring instrument;

FIG. 9A is a table showing some of the results of computations for determining the focusing position of excitation light of the embodiment of measuring instrument;

FIG. 9B is a table also showing some of the results of computations for determining the focusing position of excitation light of the embodiment of measuring instrument; and FIG. 9C is a table also showing some of the results of computations for determining the focusing position of excitation light of the embodiment of measuring instrument.

DETAILED DESCRIPTION OF THE PREFERRED EMBODIMENTS

Figure 1:
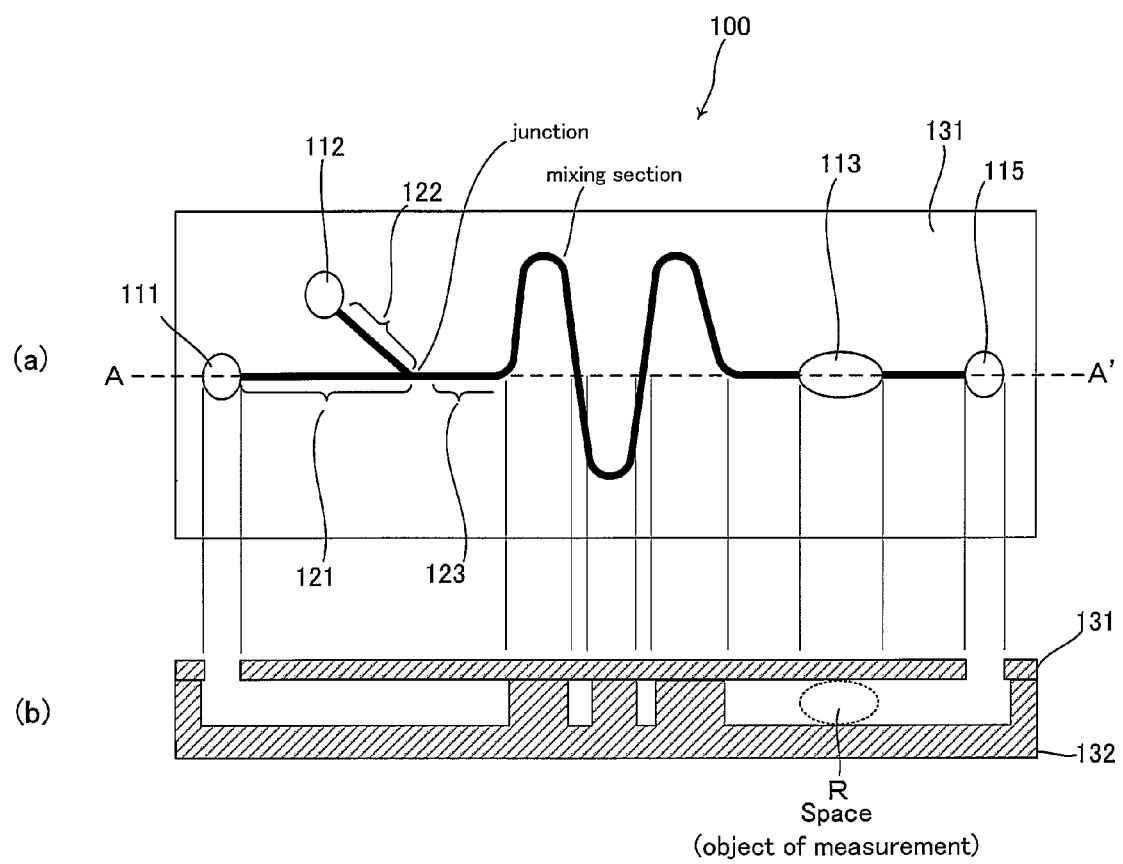
FIG. 1 is a schematic illustration of a microchip that is used for an embodiment of measuring instrument according to the present invention.

Now, preferred embodiments of the present invention will be described in greater detail by referring to the accompanying drawings. FIG. 1 is a schematic illustration of a microchip that is used for an embodiment of measuring instrument according to the present invention. FIG. 1A shows a schematic top view of the microchip, showing also the flow channel formed in the microchip. FIG. 1B shows a schematic cross-sectional view of the microchip taken along line A-A' in FIG. 1A.

The microchip 100 is formed by using a first substrate 131 and a second substrate 132. The first substrate 131 and the second substrate 132 are bonded to each other. A first liquid introducing port 111, a second liquid introducing port 112 and a discharge port 115 are formed on the first substrate 131.

A first flow channel 121, a second flow channel 122 and a third flow channel 123 are formed on the second substrate 132. The flow channels are linked to each other at one of the opposite ends of each of them to form trifurcation. The other end of the first flow channel 121 is linked to the first liquid introducing port 111 for introducing first liquid. The other end of the flow channel 122 is linked to the second liquid introducing port 112 for introducing second liquid. The first liquid and the second liquid are mixed in a mixing section of the third flow channel 123. A detecting section 113 is arranged in the third flow channel 123 and provided with a space R. The space R is the object of measurement of the measuring instrument. The other end of the third flow channel 123 is linked to the discharge port 115. The mixture of the first liquid and the second liquid is discharged from the discharge port 115.

The first substrate and the second substrate can be prepared by injection molding of injecting a resin material into respective silicon molds. Examples of resin materials that can be used for preparing the substrates include polystyrene (PS) and acryl resin (PMMA).

The microchip 100 can be prepared by applying known semiconductor processing techniques. For example, grooves are formed as flow channels on a silicon substrate by means of a micro processing technique such as anisotropic etching. Subsequently, a cover member is bonded onto the substrate to cover the grooves. Techniques of preparing a microchip 100 from a glass substrate are also known.

Typical dimensions of a microchip 100 include external dimensions of about 80 mm×60 mm×2.5 mm. The flow channels are about 0.5 mm wide and about 1 mm deep.

A sample and a reagent are introduced respectively to the first liquid introducing port 111 and the second liquid introducing port 112 of the microchip 100. The sample and the reagent are merged at the junction. The mixed liquid is further mixed in the third flow channel 123 to cause a predetermined chemical reaction to take place. The predetermined chemical reaction is observed in the space R by means of the measuring instrument.

When the microchip 100 is applied to an immunological examination, a label antibody (a fluorescent substance) is added to the sample. By doing so, the examination can utilize an antigen-antibody reaction. In the examination, excitation light is irradiated into the space R and the quantity of fluorescent light or emitted light that is generated in response to the irradiation of excitation light is measured by the optical measuring device. For example, fluorescent light of about 515 nm will be generated when the sample is marked by a label antibody, to which fluorescein is linked, and irradiated with excitation light of 495 nm.

Now, the measuring instrument of this embodiment will be described by way of an instance of measuring the intensity of fluorescent light that the fluorescent substance in a sample liquid emits, using a microchip 100.

First Embodiment

Figure 2:
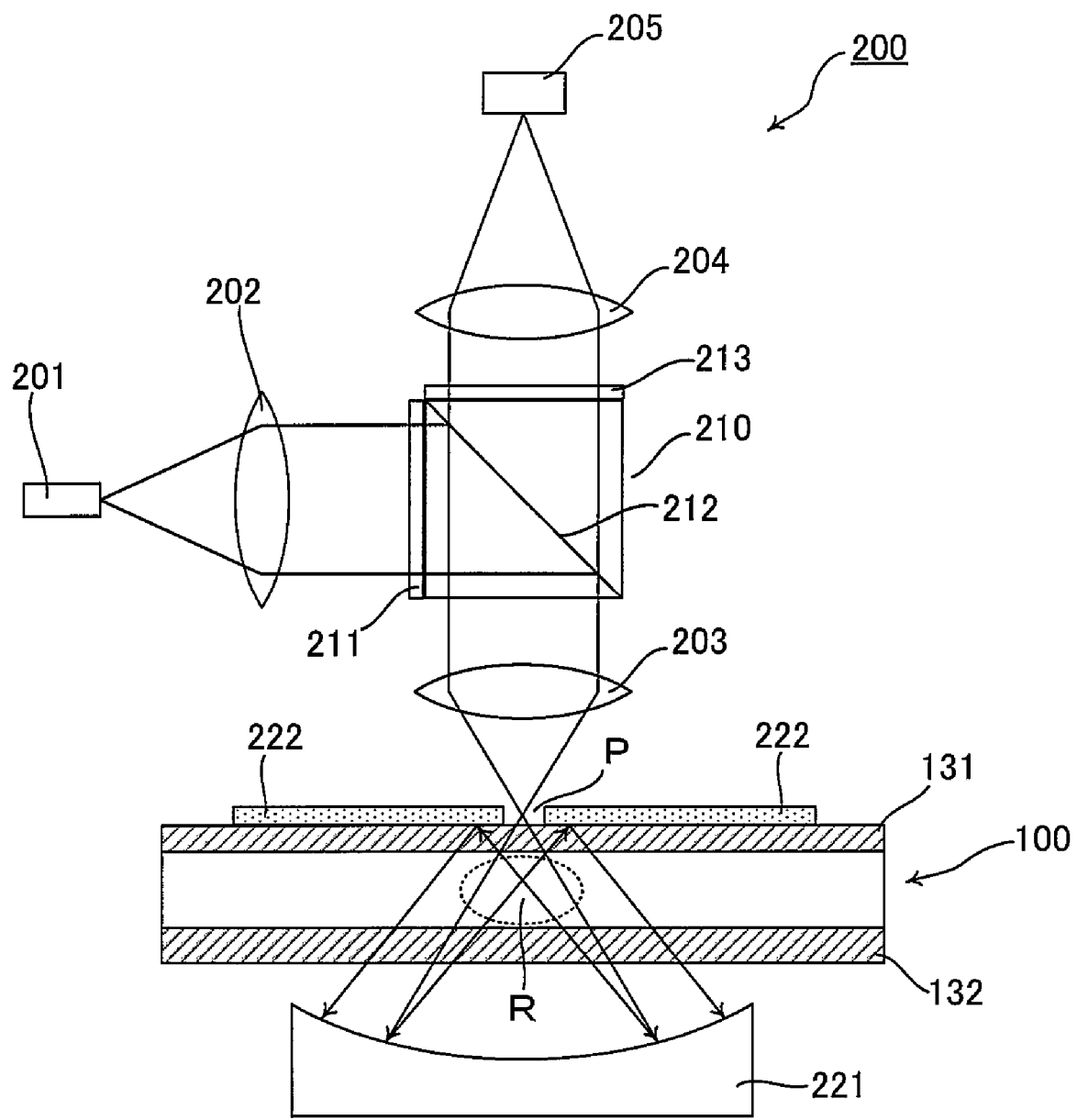
FIG. 2 is a schematic illustration of a measuring optical system of the embodiment of measuring instrument according to the present invention, including a cross-sectional view of a detecting section thereof.

FIG. 2 is a schematic illustration of a measuring optical system of the embodiment of measuring instrument according to the present invention, including a cross-sectional view of the detecting section (the space R) thereof. A microchip 100 is set in position in the measuring instrument 200 illustrated in FIG. 2. The measuring instrument 200 observes the space R in the microchip 100.

The measuring instrument 200 includes a light source 201, a collimator lens 202, an objective lens 203, a focusing lens 204, a measuring device 205, a fluorescence mirror unit 210, an excitation light selection filter 211, a dichroic mirror 212, a measuring light selection filter 213, a first mirror 221 and a second mirror 222.

The light source 201 emits light including rays of light of the wavelength of excitation light. The light source 201 may be selected from a halogen lamp, a mercury lamp, a laser, a laser diode and an LED.

The collimator lens 202 collimates light emitted from the light source 201. The collimator lens 202 may be omitted when collimated light is emitted from the light source 201.

The fluorescence mirror unit 210 includes the excitation light selection filter 211, the dichroic mirror 212 and the measuring light selection filter 213. The fluorescence mirror unit 210 separates fluorescent light from excitation light.

The excitation light selection filter 211 selects a wavelength of light passing through the space R. More specifically, it selectively transmits a wavelength that is optimum relative to the object of measurement. An optimum wavelength is the wavelength of excitation light that excites the fluorescent substance introduced into the microchip 100.

The dichroic mirror 212 reflects excitation light transmitted through the excitation light selection filter 211 to a predetermined direction and selectively transmits fluorescent light emitted from the object of measurement.

The measuring light selection filter 213 does not transmit any light of the wavelength of excitation light (in other words, limits transmission of light of the wavelength of excitation light) but transmits light of the wavelength of fluorescent light generated from the object of measurement.

The objective lens 203 focuses excitation light isolated by the fluorescence mirror unit 210 and also focuses fluorescent light generated from the object of measurement.

The focusing lens 204 focuses light transmitted through the measuring light selection filter 213 to the measuring device 205.

The measuring device 205 measures fluorescent light focused by the focusing lens 204. A photodiode or a photomultiplier can be used for the measuring device.

The first mirror 221 has a curved surface having the center of curvature at the side of the objective lens 203 (at the side of the second mirror 222) (and hence is a concave mirror). The center of curvature of the first mirror 221 is located on the optical axis of the objective lens 203. The focal length of the first mirror 221 is f.

The second mirror 222 is a plane mirror that is arranged perpendicularly relative to the optical axis of the objective lens 203. The second mirror 222 is arranged between the objective lens 203 and the first mirror 221. The mirror surface of the second mirror 222 is disposed to face the mirror surface of the first mirror 221. The second mirror 222 has an aperture P at the focusing position of the objective lens 203. More specifically, the focusing position of the objective lens 203 is located on the mirror surface of the second mirror 222.

The space R of the microchip 100 is arranged between the first mirror 221 and the second mirror 222.

Excitation light from the light source 201 sequentially enters the collimator lens 202, the excitation light selection filter 211, the dichroic mirror 212, the objective lens 203 and the aperture P in this order.

After passing through the aperture P, excitation light then passes through the microchip 100 and is subsequently reflected by the first mirror 221. Excitation light reflected by the first mirror 221 is then focused in the space R.

Excitation light is partly absorbed in the space R and converted into fluorescent light. Excitation light that is not absorbed in the space R then passes through the microchip 100 and is subsequently reflected by the second mirror 222. Excitation light reflected by the second mirror 222 is then reflected again by the first mirror 221. Excitation light reflected by the first mirror 221 for the second time is then focused in the space R.

In this way, excitation light is repeatedly reflected by the first mirror 221 and the second mirror 222 so as to be focused at a plurality of points in the space R.

Fluorescent light generated in the space R sequentially enters the aperture P, the objective lens 203, the fluorescence mirror unit 210, the focusing lens 204 and the measuring device 205.

As the sample in the microchip 100 is irradiated by excitation light in this way, fluorescent light is generated from the fluorescent substance in the sample. Generated fluorescent light is then received by the measuring device 205 by way of the fluorescence mirror unit 210. Excitation light that is reflected by the first mirror 221 and subsequently made to pass through the aperture P is blocked by the measuring light selection filter 213 and hence it does not enter the measuring device 205.

Thus, in this embodiment, the aperture P is arranged at the focusing position of the objective lens 203 so that excitation light focused by the objective lens 203 can pass through the aperture P of the second mirror 222 without any loss. Further, the aperture P is arranged at the focusing position of the objective lens 203 so that the aperture P can be formed small. Therefore, the quantity of excitation light that passes through the aperture P of the second mirror 222 can be reduced without giving rise to any adverse effect. Fluorescent light that passes through the aperture P of the second mirror 222 is also focused by the objective lens 203 efficiently. Therefore, faint fluorescent light can be excited and detected efficiently.

Now, excitation light that passes through the aperture P and enters the microchip 100 will be described more specifically.

Figure 3:
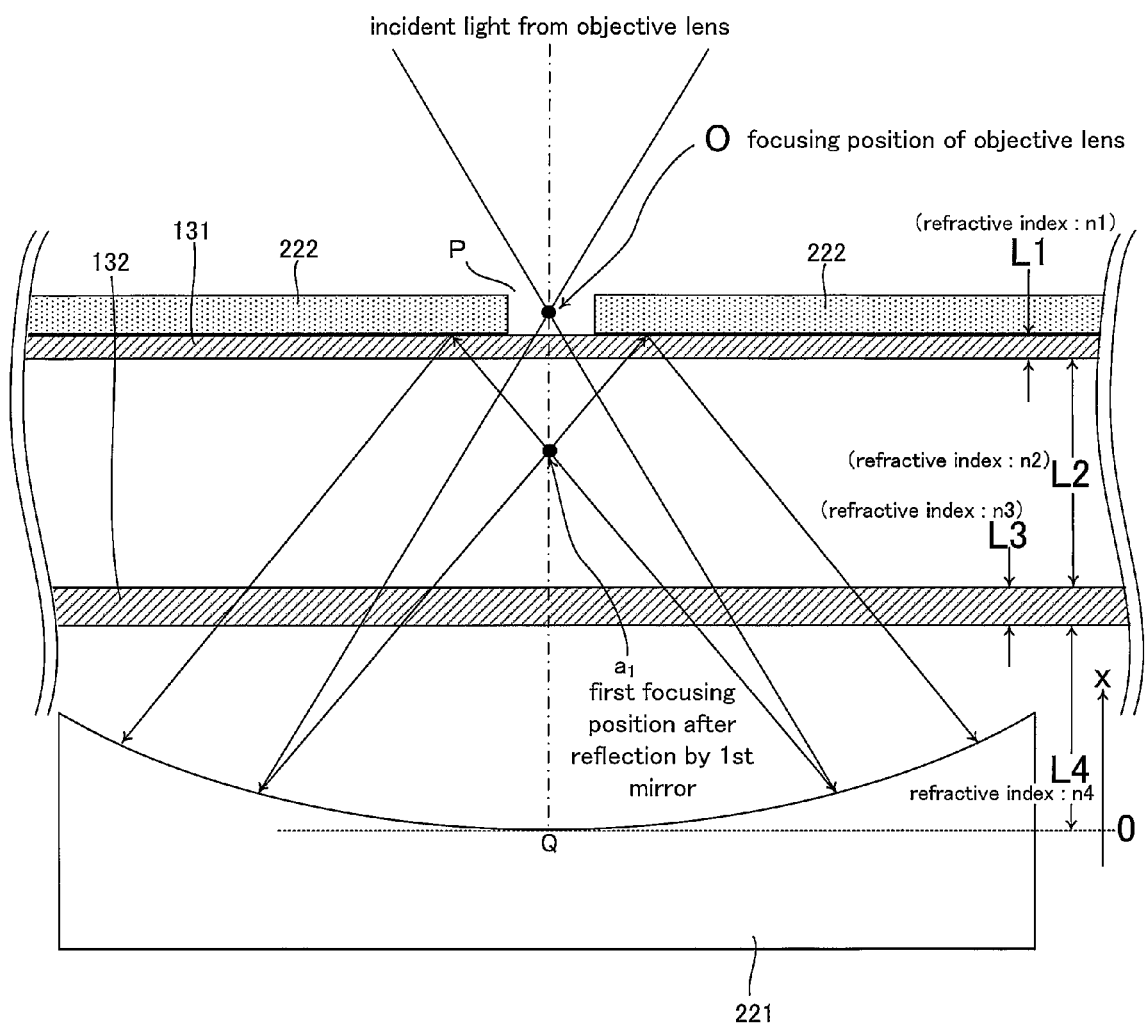
FIG. 3 is a schematic illustration of the detecting section of the embodiment of measuring instrument, showing major dimensions thereof.

FIG. 3 is a schematic illustration of some of the components of the measuring instrument 200 of this embodiment arranged near the first mirror 221 and the second mirror 222 (near the detecting section 113 of the microchip 100), showing major dimensions thereof. The members same as those described above are denoted respectively by the same reference symbols. Reference symbol O denotes the focusing position of the objective lens 203. Reference symbol Q denotes the point of intersection of the optical axis of the objective lens 203 and (the mirror surface of) the first mirror 221.

The first substrate 131 has a thickness of L1 and is made of a substance showing a refractive index of n1. The distance between the surface of the first substrate 131 at the side of the first mirror 221 and the surface of the second substrate 132 at the side of the second mirror 222 is L2 (the vertical length of the space R in FIG. 3). In a measuring process, the gap between the first substrate 131 and the second substrate 132 is filled with a sample showing a refractive index of n2. The second substrate 132 has a thickness of L3 and is made of a substance showing a refractive index of n3. The distance between the surface of the second substrate 132 at the side of the first mirror 221 and the point Q is L4. The gap between the second substrate 132 and the first mirror 221 is filled with a medium showing a refractive index of n4. If the medium between the second substrate 132 and the first mirror 221 is air, n4=1.

The distance from the distance L1 to the distance L4 is expressed by way of x-axis extending vertically in FIG. 3, of which the positive side is the upside (the side of the second mirror 222) making the height of the plane of the most convex part (point Q) of the first mirror 221 zero.

The sample is preferably a fluid such as an aqueous solution.

As described above, excitation light that passes through the aperture P then passes through the microchip 100 and is reflected by the first mirror 221. Excitation light that is reflected by the first mirror 221 is then focused to focus point $a_1$ in the space R. The fluorescent substance in the sample emits fluorescent light at the focus point $a_1$. Light focused to focus point $a_1$ is then reflected by the second mirror 222 and gets to the first mirror 221. Excitation light that gets to the first mirror 221 is then reflected again and focused to focus point $a_2$. In other words, excitation light generates fluorescent light also at position $a_2$. Note that the position $a_2$ is located close to the point Q relative to the position $a_1$.

In this way, excitation light that enters through the aperture P is reflected for a number of times by the first mirror 221 and the second mirror 222. Since the microchip 100 is arranged between the first mirror 221 and the second mirror 222, excitation light is focused, changing the position of focus point in the space R that is contained in the microchip 100. Thus, when the sample is arranged in the space R, it is irradiated with excitation light for a number of times.

Therefore, the measuring instrument 200 of this embodiment can generate fluorescent light at a plurality of points in the sample so that it can observe faint light (e.g., fluorescent light). Since fluorescent light is generated at a number of points, the intensity of fluorescent light is boosted to make it possible to achieve a high fluorescence S/N value if a sample showing a low concentration of fluorescent substance needs to be measured. Additionally, as the intensity of fluorescent light is boosted, the time necessary for a measurement can be reduced.

Still additionally, fluorescent light can be generated by excitation highly efficiently because the sample is excited by excitation light for a number of times as excitation light is focused for so many number of times in the sample. Then, the positions of the focus points $a_1$, $a_2$, ..., differ from each other on the optical axis to give rise to a net effect of multipoint detection. Multipoint detection can reduce the influence of uneven concentration and that of uneven concentration gradient, if any, of the fluorescent substance in the measuring process.

Now, the focusing conditions of this embodiment will be discussed below by referring to diagrams of optical paths of transmitted light between the first mirror 221 and the second mirror 222. FIGS. 4A through 4E are schematic illustrations of optical paths of light being transmitted along a cross section of the detecting section 113 of the detecting section 113 of the measuring instrument 200 of this embodiment. In FIGS. 4A through 4E, O=O'=O" indicate the position of the aperture P of the second mirror 222 and f indicates the focal length of the first mirror 221, while L indicates the air-equivalent length between the surface of the first substrate 131 at the side of the second mirror 222 and the point Q. Thus, $$L=L1/n1+L2/n2+L3/n3+L4/n4 \quad (1).$$

$a_n$ indicates the n-th focusing position. The vertical bidirectional arrows indicate the first mirror 221.

Figure 4A:
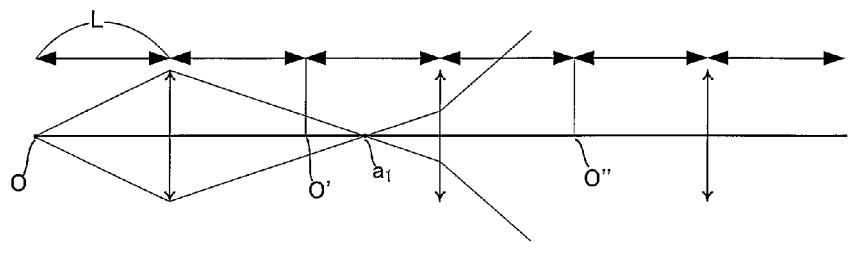
FIG. 4A is a schematic illustration of optical paths of light being transmitted along a cross section of the detecting section of the embodiment of measuring instrument.
Figure 4B:
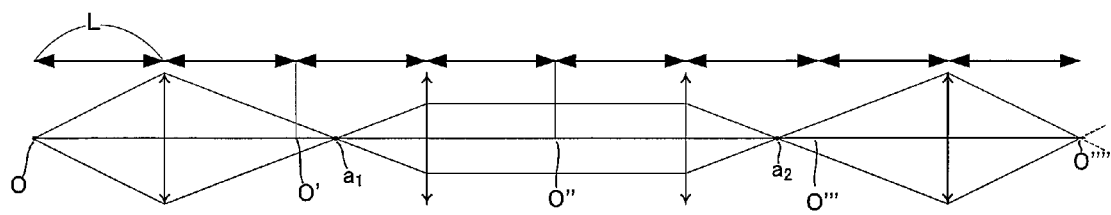
FIG. 4B is a schematic illustration of other optical paths of light being transmitted along a cross section of the detecting section of the embodiment of measuring instrument.
Figure 4C:
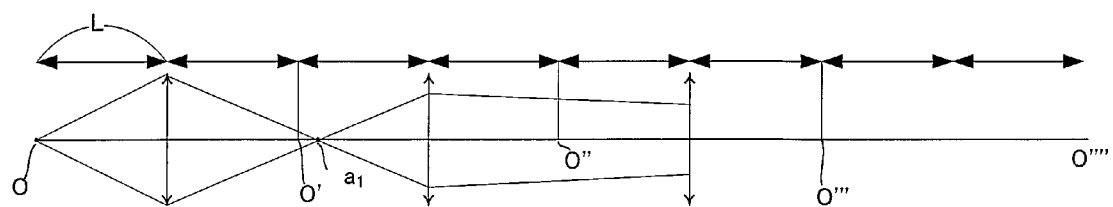
FIG. 4C is a schematic illustration of still other optical paths of light being transmitted along a cross section of the detecting section of the embodiment of measuring instrument.
Figure 4D:
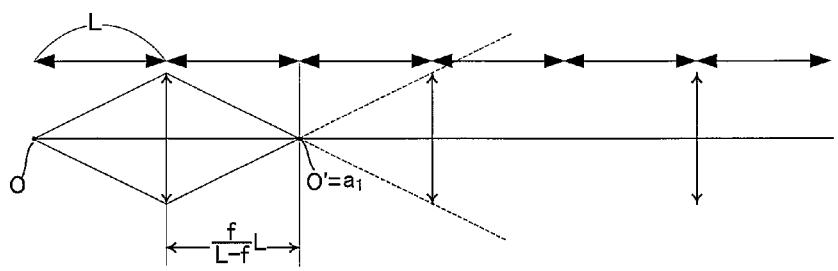
FIG. 4D is a schematic illustration of still other optical paths of light being transmitted along a cross section of the detecting section of the embodiment of measuring instrument.
Figure 4E:
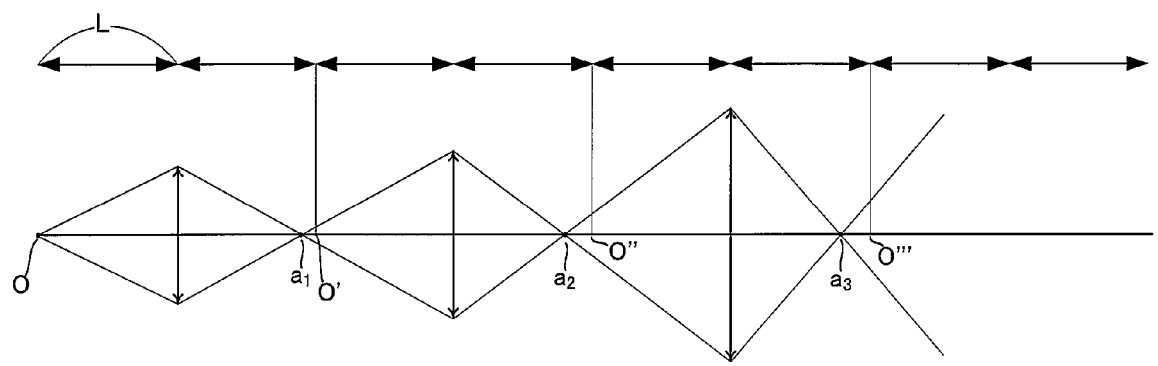
FIG. 4E is a schematic illustration of still other optical paths of light being transmitted along a cross section of the detecting section of the embodiment of measuring instrument.

FIG. 4A shows the optical paths that are observed when $(2-\sqrt{2})L<f<L$ (the first instance). FIG. 4B shows the optical paths that are observed when $f=(2-\sqrt{2})L$ (the second instance). FIG. 4C shows the optical paths that are observed when $L/2<f<(2-\sqrt{2})L$ (the third instance). FIG. 4D shows the optical paths that are observed when $L/2=f$ (the fourth instance). FIG. 4E shows the optical paths that are observed when $0<f<L/2$ (the fifth instance).

Note that excitation light reflected by the first mirror 221 is convergent light only when the requirement of f<L is satisfied. Then, therefore, excitation light is focused and can efficiently excite faint fluorescent light that can be generated in the sample.

The reason for this will be described below. If the light source is located at the aperture P of the second mirror 222 and the distance between the position where excitation light reflected by the first mirror 221 is focused and the point Q is $a_1$, $$a_1=Lf/(L-f) \quad (2)$$

from the Newton's equation.

Then, $a_1>0$ when the above requirement of f<L is satisfied. This means that excitation light that passes through the aperture of the second mirror 222 is reflected by the first mirror 221 to become convergent light.

Each of the above instances will be described by referring to FIGS. 4A through 4E showing diagrams of optical paths of transmitted light.

instance of $(2-\sqrt{2})L<f<L$: (the first instance)

Light coming out from the focusing position O of the aperture P is reflected by the first mirror 221 that is separated from the aperture P by distance L. Light reflected by the first mirror 221 is then reflected by the second mirror 222. The position of reflection at this time is indicated by O' in the drawings. Light reflected by the second mirror 222 is focused at $a_1$ in the drawings. Then, light focused aa $a_1$ is reflected again by the first mirror 221. Light reflected by the first mirror 221 is diverged.

instance of $f=(2-\sqrt{2})L$: (the second instance)

Light coming out from the focusing position O of the aperture P is reflected by the first mirror 221 that is separated from the aperture P by distance L. Light reflected by the first mirror 221 is then reflected by the second mirror 222. The position of reflection at this time is indicated by O' in the drawings. Light reflected by the second mirror 222 is focused at $a_1$ in the drawings. Then, light focused at $a_1$ is reflected again by the first mirror 221. Light reflected by the first mirror 221 is collimated and then reflected again by the second mirror 222. The position of reflection at this time is indicated by O" in the drawings. Light reflected by the second mirror 222 is reflected by the first mirror 221 and subsequently focused to $a_2$. Light is then reflected sequentially by the second mirror 222 and the first mirror 221 and focused at aperture position O"" so that it goes out from the aperture of the second mirror 222.

instance of $L/2<f<(2-\sqrt{2})L$: (the third instance)

Light coming out from the focusing position O of the aperture P is reflected by the first mirror 221 that is separated from the aperture P by distance L. Light reflected by the first mirror 221 is then reflected by the second mirror 222. The position of reflection at this time is indicated by O' in the drawings. Light reflected by the second mirror 222 is focused at $a_1$ in the drawings. Then, light focused at $a_1$ is reflected again by the first mirror 221. Light reflected by the first mirror 221 is reflected again by the second mirror 222. The position of reflection at this time is indicated by O". Light reflected by the second mirror 222 is reflected by the first mirror 221. Light reflected by the second mirror 222 is not focused until it is reflected by the first mirror 221. In other words, excitation light that is focused after being reflected by the first mirror 221 and the second mirror 222 has to be reflected by the first mirror 221 for a number of times before it is focused.

instance of $L/2=f$: (the fourth instance)

Light coming out from the focusing position O of the aperture P is reflected by the first mirror 221 that is separated from the aperture P by distance L. Light reflected by the first mirror is focused at aperture position O' so that it goes out from the aperture of the second mirror 222.

instance of $0<f<L/2$: (the fifth instance)

Light coming out from the focusing position O of the aperture P is reflected by the first mirror 221 that is separated from the aperture P by distance L. Light reflected by the first mirror 221 is then focused at $a_1$. Light focused at $a_1$ is then reflected by the second mirror 222. The position of reflection at this time is indicated by O'. Light reflected by the second mirror 222 is reflected again by the first mirror 221. Light reflected by the first mirror 221 is focused at $a_2$ in the drawings. Light focused at $a_2$ is then reflected again by the second mirror 222. The position of reflection at this time is indicated by O" in the drawings. Light reflected by the second mirror 222 is then reflected again by the first mirror 221 so that it is reflected further repeatedly.

Here, the distance between $a_1$ and O" is longer than the distance between $a_2$ and O'. Similarly, the distance between $a_3$ and O''' is longer than the distance between $a_2$ and O".

As seen from the diagrams of optical paths of transmitted light, particularly when the requirement of $0<f>L/2$ is satisfied, excitation light passing through the aperture of the second mirror 222 is reflected by the first mirror 221 and subsequently focused before it gets to the second mirror 222. Additionally, excitation light is focused at a number of points as it is repeatedly reflected by the first mirror 221 and the second mirror 222. Thus, faint fluorescent light from the sample can be excited efficiently.

When the requirement of $0<f<L/2$ is satisfied, excitation light is focused at $a_1$, $a_2$, ... on the optical axis. Then, excitation light is ultimately focused at predetermined positions $a_\infty$. Hereinafter the focusing positions of excitation light converge when $0<f<L/2$ is satisfied will be proven below.

Figure 5B:
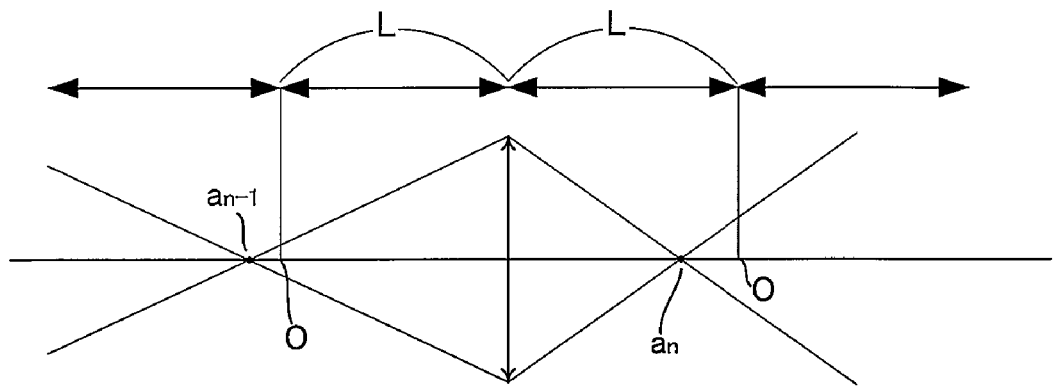
FIG. 5B is another schematic illustration of convergence of focusing positions of the embodiment of measuring instrument.
Figure 5C:
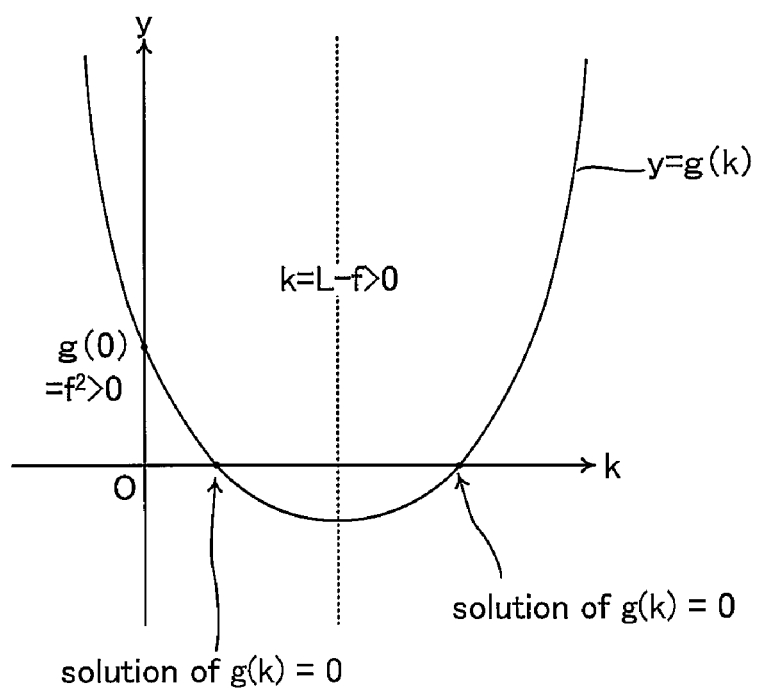
FIG. 5C is still another schematic illustration of convergence of focusing positions of the embodiment of measuring instrument.

FIGS. 5A through 5C are drawings for proving that the focusing positions of the measuring instrument 200 of this embodiment converge. FIG. 5A is a schematic illustration of convergence of focusing positions $a_1$, $a_2$, ... of the measuring instrument of this embodiment. FIG. 5B is a diagram of optical paths of transmitted light, showing the positional relationship between focusing position $a_{n-1}$ and focusing position $a_n$. FIG. 5C is a reference drawing for looking into the solution of $g(k)$, which will be described below.

Formula (3) shown below holds true because of the Newton's image formation equation when the Newton's equation is applied to focusing position $a_{n-1}$ and focusing position $a_n$.
[Formula 1]

$$(L-a_{n-1}+L-f)(a_n-f)=f^2 \quad (3)$$

Formula (4) shown below can be obtained by reorganizing the above formula for $a_n$.

[formula 2]

$$a_n = \frac{(a_{n-1}-2L)f}{a_{n-1}-2L+f} \quad (4)$$

Characteristic equation (5) is defined for determining the general term of $a_n$.

[formula 3]

$$x = \frac{(x-2L)f}{x-2L+f} \quad (5)$$

The solution of the characteristic equation (5) is expressed by formula (6) below.
[Formula 4]

$$x = L \pm \sqrt{L^2-2Lf} \quad (6)$$

Then, sequence of numbers $b_n$ is newly defined by formula (7) below.
[Formula 5]

$$b_n = a_n - (L - \sqrt{L^2-2Lf}) \quad (7)$$

Thus, $a_{n-1}$ is expressed by the formula shown below.
[Formula 6]

$$a_{n-1} = b_{n-1} + (L - \sqrt{L^2-2Lf}) \quad (8)$$

The formula shown below is obtained by using the formula (7) and the formula (8) as substitutes in the formula (4).

[formula 7]

$$b_n = \frac{b_{n-1}(f-L+\sqrt{L^2-2Lf})}{b_{n-1}-L-\sqrt{L^2-2Lf}+f} \quad (9)$$

Formula (10) shown below is obtained for the reciprocal of the formula (9).

[formula 8]

$$\frac{1}{b_n} = \frac{1}{b_{n-1}}\left(\frac{-L-\sqrt{L^2-2Lf}+f}{f-L+\sqrt{L^2-2Lf}}\right) + \frac{1}{f-L+\sqrt{L^2-2Lf}} \quad (10)$$

Furthermore, as sequence of numbers $c_n$ is defined by formula (11) below, the formula (10) can be rewritten to read as formula (12).

[formula 9]

$$c_n \equiv \frac{1}{b_n} \quad (11)$$

[formula 10]

$$c_n = c_{n-1}\left(\frac{-L-\sqrt{L^2-2Lf}+f}{f-L+\sqrt{L^2-2Lf}}\right) + \frac{1}{f-L+\sqrt{L^2-2Lf}} \quad (12)$$

Now, $\alpha$ that satisfies the requirement of formula (13) below is determined to determine the general term of the sequence of numbers $c_n$.

[formula 11]

$$c_n - \alpha = \left(\frac{L-f+\sqrt{L^2-2Lf}}{L-f-\sqrt{L^2-2Lf}}\right)(c_{n-1}-\alpha) \quad (13)$$

Then, from the formulas (12) and (13), α can be expressed by formula (14) below.

[formula 12]

$$a = \frac{1}{2\sqrt{L^2-2Lf}} \quad (14)$$

Formula (15) below can be obtained by using the formula (13)

[formula 13]

$$\frac{c_n-\alpha}{c_{n-1}-\alpha} \cdot \frac{c_{n-1}-\alpha}{c_{n-2}-\alpha} \cdots \frac{c_2-\alpha}{c_1-\alpha} = \left(\frac{L-f+\sqrt{L^2-2Lf}}{L-f-\sqrt{L^2-2Lf}}\right)^{n-1} \quad (15)$$

Thus, the general term of $c_n$ can be expressed by formula (16) below.

[formula 14]

$$c_n = (c_1-\alpha)\left(\frac{L-f+\sqrt{L^2-2Lf}}{L-f-\sqrt{L^2-2Lf}}\right)^{n-1} + \alpha \quad (16)$$

Then, the general term of $b_n$ can be expressed by formula (17) below.

[formula 15]

$$b_n = \frac{1}{(c_1-\alpha)\left(\frac{L-f+\sqrt{L^2-2Lf}}{L-f-\sqrt{L^2-2Lf}}\right)^{n-1} + \alpha} \quad (17)$$

Furthermore, the general term of $a_n$ can be expressed by formula (18) below.

[formula 16]

$$a_n = \frac{1}{(c_1-\alpha)\left(\frac{L-f+\sqrt{L^2-2Lf}}{L-f-\sqrt{L^2-2Lf}}\right)^{n-1} + \alpha} + L - \sqrt{L^2-2Lf} \quad (18)$$

Therefore, $c_1$ is expressed by formula (19) below.

[formula 17]

$$c_1 = \frac{1}{b_1} = \frac{L-f}{-L^2+2Lf+(L-f)\sqrt{L^2-2Lf}} \quad (19)$$

Now, that formula (20) below holds true will be proved to make sure that the formula (18) expressing the general term of $a_n$ converges.

[Formula 18]

$$L-f-\sqrt{L^2-2Lf}=k>0 \quad (20)$$

The formula (20) is rewritten so as to read as formula (21) below and the two sides are squared.

[Formula 19]

$$L-f-k=\sqrt{L^2-2Lf} \quad (21)$$

The formula (21) is "equivalent to formula (22) and to formula (23)".

[Formula 20]

$$(L-f-k)^2 = L^2-2Lf \quad (22)$$

[Formula 21]

$$L-f-k>0 \quad (23)$$

The equation (22) is solved for k to obtain formula (24) below.

[Formula 22]

$$k^2+(2f-2L)k+f^2=0 \quad (24)$$

Now, function g(k) of k is defined by formula (25) below.

[Formula 23]

$$g(k)=k^2+(2f-2L)k+f^2 \quad (25)$$

This means that the solution to g(k)=0 is k.
Formula (26) below is discriminant D of the formula (24).

[Formula 24]

$$D=4f^2-8fL+4L^2-4f^2=4L(L-2f) \quad (26)$$

D>0 because L>0 and 0<f<L/2. In other words, there are two solutions that satisfy g(k)=0.

Now, the formula (25) is deformed so as to read as formula (27) below.

[Formula 25]

$$g(k)=\{k-(L-f)\}^2-L^2+2Lf \quad (27)$$

Since f<L, the axis of the function g(k) is positive.
Additionally, g(0) is determined by formula (28) below.

[Formula 26]

$$g(0)=f^2>0 \quad (28)$$

FIG. 5C shows y=g(k) expressed on k-y plane.
FIG. 5C is a graph expressing y=g(k) on k-y plane. The graph of the function g(k) is downwardly projecting and both the central axis thereof and g(0) show a positive value. Thus, the solutions that satisfy g(k)=0 are all positive. Therefore, the formula (20) is true.

The inside of the parentheses of the denominator of the first term of the formula (18) is larger than 1 as proved by formula (29) below because the formula (20) is true.

[formula 27]

$$\left(\frac{L-f+\sqrt{L^2-2Lf}}{L-f-\sqrt{L^2-2Lf}}\right)^{n-1} = \left(1+\frac{2\sqrt{L^2-2Lf}}{L-f-\sqrt{L^2-2Lf}}\right)^{n-1} > (1)^{n-1} \quad (29)$$

Thus, the first term of the formula (18) converges as n approaches the infinite or n→∞ that consequently the formula (18) converges to formula (30) below as n approaches the infinite.

[Formula 28]

$$a_\infty = L - \sqrt{L^2 - 2Lf} \quad (30)$$

Additionally, $a_{n-1} > a_n$ holds true on the basis of the formula (18).

As described above, the requirement of $a_{n-1} > a_n$ is satisfied as long as the requirement of $0 < f < L/2$ is satisfied and the focusing positions $a_1, a_2, \ldots$ of excitation light are found on the same optical axis. The focusing position of excitation light is expressed by the formula (30) when $a_\infty$. Thus, the focusing positions of excitation light are monotonously converged.

Therefore, excitation light is focused for a number of times (infinite times) in the sample that is placed in the space R in the microchip 100 as it is repeatedly reflected by the first mirror 221 and the second mirror 222.

Thus, the sample is excited for a plurality of times (infinite times) by excitation light to make it possible to observe faint light (e.g., fluorescent light). Additionally, the fact that the focusing positions $a_1, a_2, \ldots$ of excitation light are different from each other on the same optical axis means that the operation is an operation of multipoint detection.

Consequently, if an uneven concentration and/or an uneven concentration gradient exist in the sample, the influence of uneven concentration and that of uneven concentration gradient can be reduced because of the multipoint detection.

Now, the results of a simulation of determining the focusing positions $a_1, a_2, \ldots$ of excitation light when the requirement of $f < L/2$ is satisfied will be described below. FIGS. 9A through 9C are tables showing the results of an operation of computationally determining focusing positions of excitation light by the measuring instrument 200 of this embodiment. FIG. 9A shows positions, materials (mediums), gaps separating the materials (mediums), refractive indexes and air-equivalent lengths of each member. FIG. 9B shows the focal length of the first mirror 221. FIG. 9C shows the results of the simulation of determining the focusing positions $a_1, a_2, \ldots$ of excitation light.

As shown in FIG. 9A, the first substrate 131 of the microchip 100 is made of PS (polystyrene) and has a thickness of L1=0.5 mm and a refractive index of n1=1.59. Thus the air-equivalent length thereof is 0.314 mm.

The space R is filled with a sample having a refractive index of n2=1.33. The distance between the surface of the first substrate 131 at the side of the first mirror 221 and the surface of the second substrate 132 at the side of the second mirror 222 is L2=1.00 mm. Thus, the air-equivalent length thereof is 0.752 mm.

The second substrate 132 is made of PS (polystyrene) and has a thickness of L3=1.0 mm and a refractive index of n3=1.59. Thus the air-equivalent length thereof is 0.629 mm.

The distance between the surface of the second substrate 132 at the side of the first mirror 221 and the point Q is L4=1.0 mm and air having a refractive index of n4=1 exists in the gap. Thus, the air-equivalent length thereof is 1 mm.

The second mirror 222 and the first substrate 131 is held in tight contact with each other. The air-equivalent length L between the first mirror 221 and the second mirror 222 (the distance between the surface of the first substrate 131 at the side of the second mirror 222 and the point Q) is 2.695 mm.

As shown in FIG. 9B, the focal length f=1.213 of the first mirror 221 is selected so as to be 0.45 times of the air-equivalent length L. Thus, the requirement of $f < L/2$ is satisfied.

The focusing positions are computationally determined on the above listed conditions and FIG. 9C shows the results of the computations. As shown in FIG. 9C, the focusing positions $a_1=2.205$ mm, $a_2=1.959$ mm ... gradually decrease to converge to $a_\infty=1.843$ mm. Thus, the results of the simulation agree with the outcome of the formula (30).

Now, the conditions that are determined by taking the materials of the microchip 100 and the type of the sample into consideration will be described below.

In this embodiment, the sample needs to be placed at a position located on the optical axis at the side of the second mirror 222 relative to the point Q and separated from the point Q by a distance of $Lf/(L-f)$. In other words, the sample needs to be placed at least at the position of $a_1$. Then, as a result, the sample is excited by excitation light for a number of times (infinite times) to make it possible to observe faint light (e.g., fluorescent light) emitted from the sample. Repeat, now it is possible to observe faint light.

Additionally, as pointed out above, $a_1 > a_n > a_\infty = L - (L^2 - 2fL)^{1/2}$ holds true for the focusing positions $a_1, a_2, \ldots$ of excitation light. Therefore, the sample is preferably-placed at the side of the second mirror 222 relative to the point Q such that the distance from the point Q covers the entire range from $a_\infty$ to $a_1$. Then, as a result, the sample is excited by excitation light for a number of times (infinite times) to make it possible to observe faint light (e.g., fluorescent light) emitted from the sample. Repeat, now it is possible to observe faint light.

Preferably, the above-described embodiment satisfies the requirement of formula (31) below.

[formula 29]

$$\frac{L3}{n3} + \frac{L4}{n4} < \frac{Lf}{L-f} < \frac{L2}{n2} + \frac{L3}{n3} + \frac{L4}{n4} \quad (31)$$

When the embodiment satisfies the requirement of the formula (31), excitation light entering from the aperture P is reflected by the first mirror 221 and focused to the inside of the flow channel (the inside of the sample). Therefore, faint light emitted from the sample can be excited efficiently so that the faint light becomes observable.

Preferably, the above-described embodiment satisfies the requirement of formula (32) below.

[Formula 30]

$$L3/n3 + L4/n4 < L - \sqrt{L^2 - 2Lf} < L2/n2 + L3/n3 + L4/n4 \quad (32)$$

When the requirement of the condition formula (32) is satisfied, excitation light is repeatedly reflected by the first mirror 221 and the second mirror 222 and the focusing positions of excitation light converges to a single point of $a_\infty$ as pointed out above. Then, since excitation light is reflected for infinite times in the flow channel (in the sample) to make it possible to observe faint fluorescent light emitted from the sample. Repeat, now it is possible to observe faint light.

Now, other embodiments of the present invention will be described below.

Second Embodiment

Figure 6:
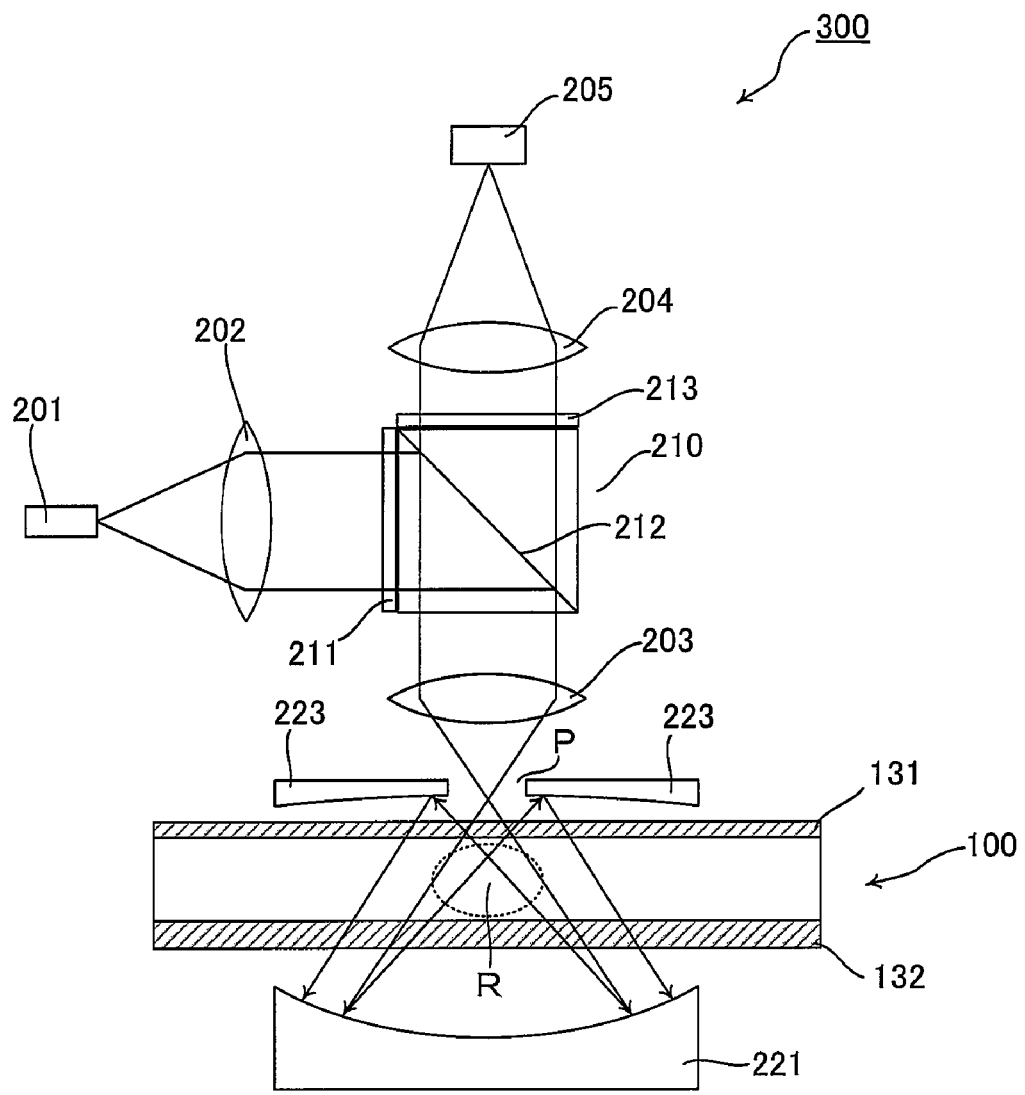
FIG. 6 is a schematic illustration of the measuring optical system of another embodiment of measuring instrument according to the present invention, including a cross-sectional view of the detecting section of thereof.

FIG. 6 is a schematic illustration of the measuring optical system of the measuring instrument 300 of this embodiment, including a cross-sectional view of the detecting section 113 (the space R) thereof. This embodiment differs from the embodiment of FIG. 2 in terms of the second mirror. The second mirror 223 of the measuring instrument 300 of this embodiment has a curved surface. Otherwise, this embodiment is same as the embodiment of FIG. 2. The members of this embodiment that are common to FIG. 1 are denoted respectively by the same reference symbols.

This embodiment provides advantages similar to those of the above-described embodiment.

Additionally, with this embodiment, the power of the first mirror 221 can be dispersed to the second mirror 223 because the second mirror 223 has a curved mirror source. Therefore, the power of the first mirror 221 can be reduced to widen the manufacturing margin thereof.

Third Embodiment

The second mirror 222 of the embodiment of FIG. 2 or the second mirror 223 of the embodiment of FIG. 6 may be replaced by a dichroic mirror. A dichroic mirror reflects excitation light and transmits fluorescent light.

Thus, with this embodiment where a dichroic mirror is employed for the second mirror (222, 223), excitation light is confined to between the first mirror 221 and the second mirror (222, 223), while fluorescent light from the sample is transmitted to the side of the measuring device 205. As a result, the measuring device can acquire a strong measurement signal. Thus, this embodiment can observe faint light.

A still another embodiment of the present invention will be described below.

Fourth Embodiment

Figure 7:
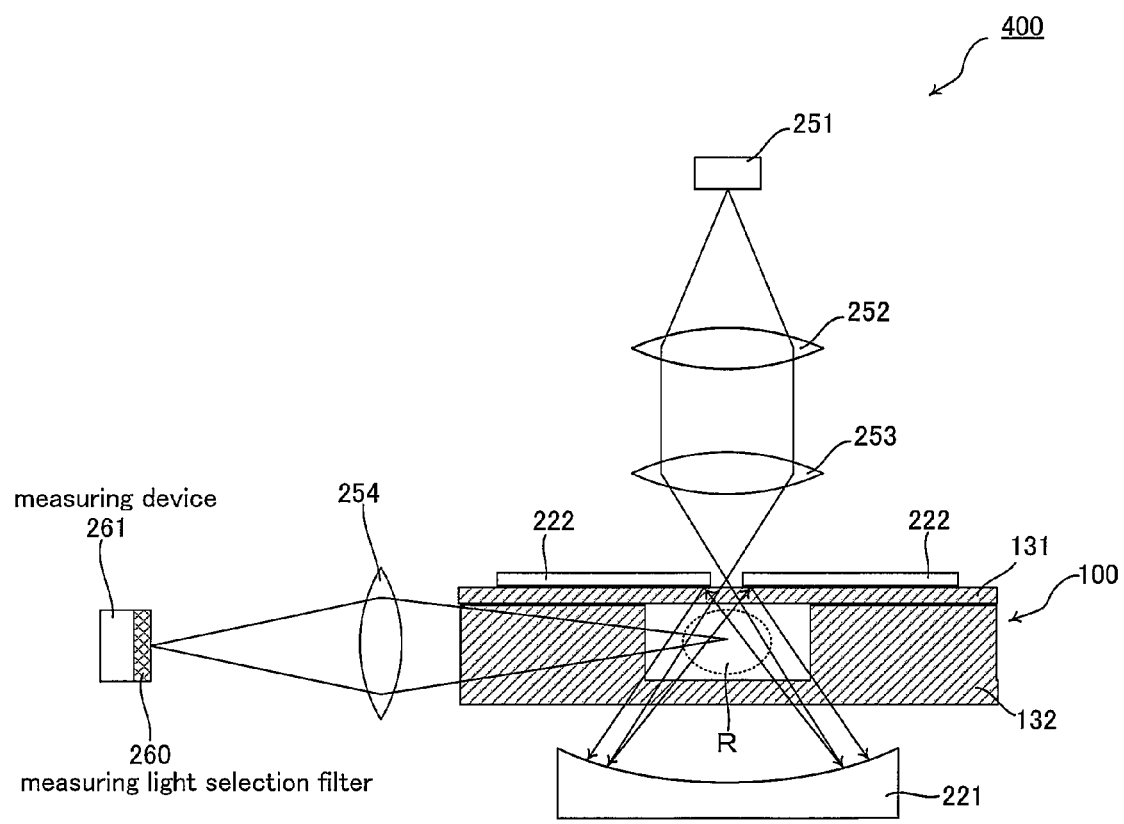
FIG. 7 is a schematic illustration of the measuring optical system of still another embodiment of measuring instrument according to the present invention, including a cross-sectional view of the detecting section of thereof.

FIG. 7 is a schematic illustration of the measuring optical system of the measuring instrument 400 of this embodiment, including a cross-sectional view of the detecting section 113 (the space R) thereof.

The light source 251 of the measuring instrument 400 of this embodiment includes a collimator lens 252, an objective lens 253, a focusing lens 254, a measuring light selection filter 260 and a measuring device 261. The components denoted by the reference symbols same as those of FIG. 2 are same as those of FIG. 2. Therefore, only the differences between these embodiments will be described below.

The light source 251 is similar to the light source 201.

The collimator lens 252 collimates light emitted from the light source 251. The collimator lens 252 may be omitted when collimated light is emitted from the light source 251.

The objective lens 253 focuses excitation light collimated by the collimator lens 252.

The focusing lens 254 focuses fluorescent light in the microchip 100 to the measuring device 261.

The measuring light selection filter 260 does not transmit any light of the wavelength of excitation light (in other words, limits transmission of light of the wavelength of excitation light) but transmits light of the wavelength of fluorescent light generated from the object of measurement.

The measuring device 261 measures fluorescent light focused by the focusing lens 254. A photodiode or a photomultiplier can be used for the measuring device 261. The measuring device 261 is arranged in a direction perpendicular to the optical axis of excitation light.

The first mirror 221 has a curved surface having the center of curvature at the side of the objective lens 253 (at the side of the second mirror 222) (and hence is a concave mirror). The center of curvature of the first mirror 221 is located on the optical axis of the objective lens 253.

The second mirror 222 is arranged perpendicularly relative to the optical axis of the objective lens 253. The second mirror 222 is arranged between the objective lens 253 and the first mirror 221. The second mirror 222 has an aperture at the focusing position of the objective lens 253.

The microchip 100 has a transparent section 116 at the lateral surface thereof.

The transparent section 116 transmits light in the space R to the outside. In other words, the transparent section 116 operates as an internal light transmitting window.

In this embodiment, excitation light irradiated from the light source 251 sequentially enters the collimator lens 252, the objective lens 253 and the aperture P. The principle of focusing light of the first mirror 221 and the second mirror 222 is same as that of the aforementioned embodiments.

In this embodiment, fluorescent light emitted from the sample existing in the space R sequentially enters the transparent section 116, the focusing lens 254, the measuring light selection filter 260 and the measuring device 261. The focusing lens 254 is arranged so as to make the focusing position $a_\infty$ of excitation light and the measuring device 261 show a conjugate positional relationship.

This embodiment provides advantages similar to those of the preceding embodiments and additionally prevents fluorescent light emitted from the sample from being cut by the second mirror 222. As a result, the measuring device 261 can detect faint light (measurement signal)

Now the method of measuring light emitted from the sample of each of the aforementioned embodiments will be described below by referring to FIG. 8.

Figure 8:
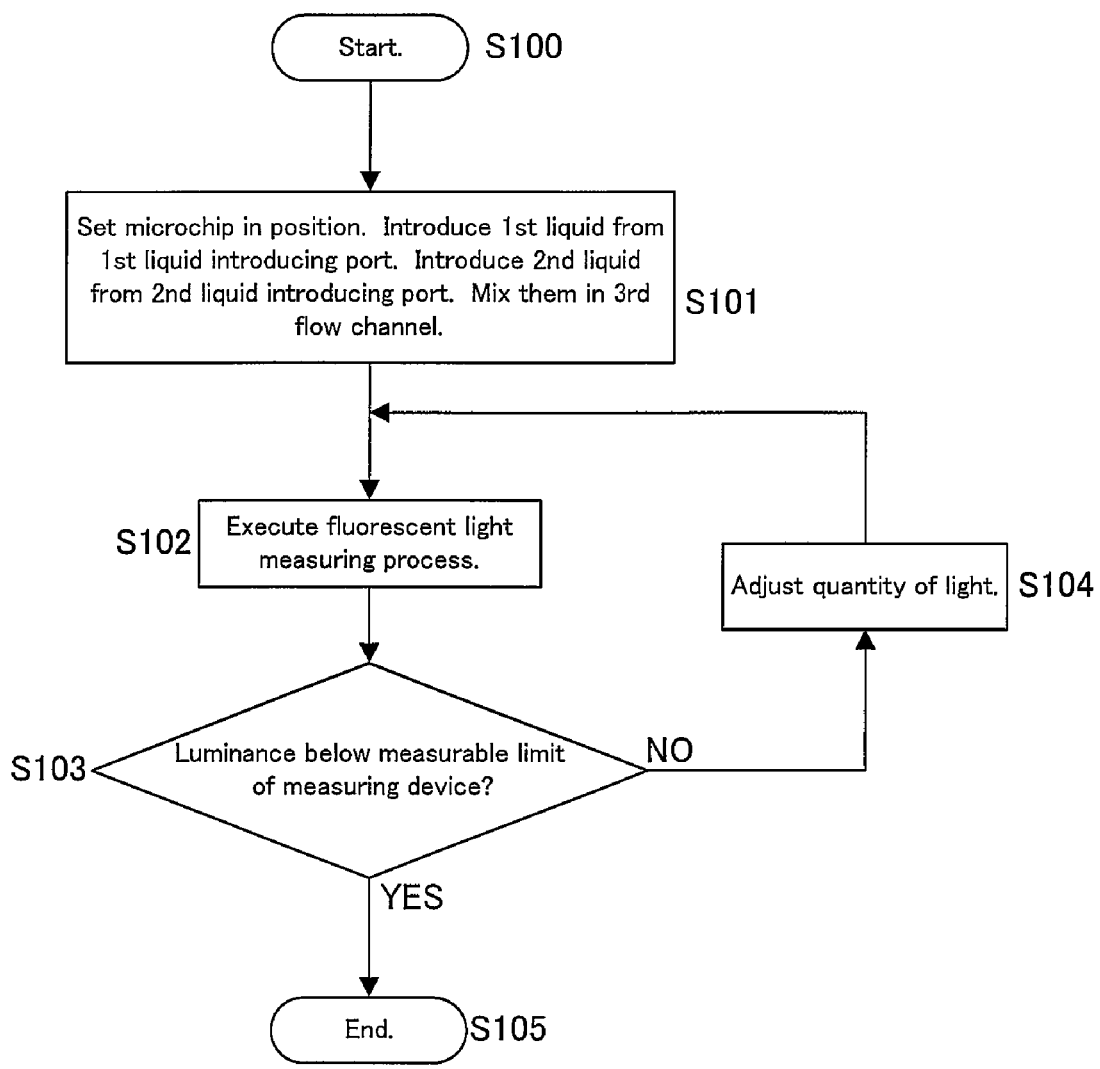
FIG. 8 is a flowchart of measuring process applicable to any embodiment of measuring instrument according to the present invention.

Referring to FIG. 8, a measuring process starts at Step S100. Subsequently, the process proceeds to Step S101, where the microchip 100 is set in position in the measuring instrument (200, 300, 400). Then, the first liquid is introduced from the first liquid introducing port 111, while the second liquid is introduced from the second liquid introducing port 112. The first liquid and the second liquid are mixed in the third flow channel 123 and the sample is introduced into the space R. In Step S102, fluorescent light radiated from the sample is measured by the measuring instrument (200, 300, 400).

In Step S103, if the measured luminance of fluorescent light lies below the measurable luminance limit (upper limit value) of the measuring device (205, 261) or not is determined.

If the answer to the question in Step S103 is YES, the process proceeds to Step S105 to end the measuring process.

If, on the other hand, the answer to the question in Step S103 is NO, the process proceeds to Step S104, where the quantity of light of the measuring system is adjusted and fluorescent light is measured again in Step S102.

Thus, the dynamic range of measurement can be increased by measuring fluorescent light, adjusting the quantity of light.

The quantity of light can be adjusted by arranging an ND filter on the measuring optical path, lowering the output of the light source if the output of the light source is variable, lowering the gain of the measuring device, reducing the exposure time of the measuring device or combining two or more than two of the above techniques.

Thus, excitation light can be focused to the sample existing in the space R for a number of times (infinite times) with any of the above-described embodiments of measuring instrument and measuring method. Therefore, the sample is excited by excitation light for a number of times (infinite times) to make it possible to observe faint light (e.g., fluorescent light).

Additionally, the intensity of fluorescent light can be boosted to achieve a high fluorescence S/N value. Still additionally, as the intensity of fluorescent is boosted, the time required for a single measuring process can be reduced.

Furthermore, as excitation light is focused for a number of times (infinite times) in the sample as described above, the sample is excited for so many number of times (infinite times) so that faint light such as fluorescent light can be excited efficiently. Additionally, the focusing positions of excitation light vary on the optical axis to give rise to a net effect of multipoint detection. Multipoint detection can reduce the influence of uneven concentration and that of uneven concentration gradient, if any, of the fluorescent substance in the measuring process.

While the present invention is described above by way of a number of embodiments, two or more than two of the embodiments may be combined appropriately and such combinations are also within the scope of the present invention.

For example, when one or more than one mirrors and/or one or more than one other optical members are interposed between the objective lens (203, 253) and the aperture P, the expression of "the optical axis of the objective lens" is paraphrased so as to read as "the optical axis of the optical member arranged optically immediately in front of the aperture P".

The measuring device of the second embodiment may be arranged perpendicularly relative to the optical axis of excitation light as in the fourth embodiment.

When a measuring instrument according to the present invention is operated as an immunological measuring instrument, it can be used to measure the tumor contained in blood serum, any of various hormones, an antibody of a pathogen of an infectious disease or the like.

What is claimed is:

1. A measuring instrument comprising:
   a light source for irradiating excitation light;
   an objective lens;
   a first mirror;
   a second mirror; and
   a measuring device, and
   the second mirror being arranged between the objective lens and the first mirror with the mirror surface of the first mirror facing the mirror surface of the second mirror;
   the first mirror having a curved surface with the center of curvature thereof disposed on the optical axis of the objective lens at the side of the second mirror; and
   the second mirror having an aperture at a position on the optical axis, the position of the aperture agreeing with the focal length of the objective lens.

2. A measuring instrument comprising:
   a light source for irradiating light including rays of light having the wavelength of excitation light;
   an objective lens for focusing light irradiated from the light source to a predetermined focusing position;
   a first mirror for reflecting light from the objective lens;
   a second mirror for reflecting light reflected by the first mirror, the second mirror having an aperture; and
   a measuring device for measuring light generated from a sample and having a wavelength different from the wavelength of excitation light, and
   the sample being arranged between the first mirror and the second mirror;
   the focusing position of the objective lens being made to agree with the position of the aperture; and
   the measuring device being adapted to measure light of a wavelength different from the wavelength of excitation light generated from the sample and passing through the aperture.

3. A measuring instrument comprising:
   a light source for irradiating light including rays of light having the wavelength of excitation light;
   an objective lens for focusing light irradiated from the light source to a predetermined focusing position;
   a first mirror for reflecting light from the objective lens;
   a second mirror for reflecting light reflected by the first mirror, the second mirror having an aperture;
   a focusing lens for focusing light generated from a sample and having a wavelength different from the wavelength of excitation light;
   a measuring device for measuring light generated from a sample and having a wavelength different from the wavelength of excitation light; and
   an excitation light cut filter arranged immediately in front of the measuring device at the light receiving side thereof to cut excitation light, and
   the sample being arranged between the first mirror and the second mirror;
   the focusing position of the objective lens being made to agree with the position of the aperture so as to make the focusing position of excitation light and the measuring device show a conjugate positional relationship; and
   the measuring device being adapted to measure light of a wavelength different from the wavelength of excitation light generated from the sample.

4. The measuring instrument according to claim 1, wherein the second mirror is a dichroic mirror.

5. The measuring instrument according to claim 1, wherein $f<L$, where the air-equivalent length between the first mirror and the second mirror is L and the focal length of the first mirror is f.

6. The measuring instrument according to claim 1, wherein $f<L/2$, where the air-equivalent length between the first mirror and the second mirror is L and the focal length of the first mirror is f.

7. The measuring instrument according to claim 1, wherein the reflection surface of the second mirror is a curved surface.

8. A measuring method comprising:
   arranging a measuring device having:
      a light source for irradiating excitation light;
      an objective lens;
      a first mirror;
      a second mirror; and
      a measuring device, and
      the second mirror being arranged between the objective lens and the first mirror with the mirror surface of the first mirror facing the mirror surface of the second mirror;
      the first mirror having a curved surface with the center of curvature thereof disposed on the optical axis of the objective lens at the side of the second mirror; and
      the second mirror having an aperture at a position on the optical axis, the position of the aperture agreeing with the focal length of the objective lens, and
   arranging a sample separated from the point of intersection of the optical axis and the first mirror by a distance of $Lf/(L-f)$ at the side of the second mirror relative to the point of intersection on the optical axis to measure light emitted from the sample;
   where L being the air-equivalent length between the first mirror and the second mirror; and
   f being the focal length of the first mirror.

9. A measuring method comprising:
   arranging a measuring device having:
      a light source for irradiating excitation light;
      an objective lens;
      a first mirror;
      a second mirror; and
      a measuring device, and the second mirror being arranged between the objective lens and the first mirror with the mirror surface of the first mirror facing the mirror surface of the second mirror;

the first mirror having a curved surface with the center of curvature thereof disposed on the optical axis of the objective lens at the side of the second mirror;

the second mirror having an aperture at a position on the optical axis, the position of the aperture agreeing with the focal length of the objective lens, and arranging a sample separated from the point of intersection of the optical axis and the first mirror by a distance of $Lf/(L-f)$ at the side of the second mirror relative to the point of intersection on the optical axis to measure light emitted from the sample; and arranging a sample at all X positions located at the side of the second mirror relative to the point of intersection on the optical axis and satisfying the requirement as defined below;

$$L-(L^2-2fL)^{1/2} \leq X \leq Lf(L-f);$$

where X being the distance from the point of intersection;
L being the air-equivalent length between the first mirror and the second mirror; and
f being the focal length of the first mirror.

10. A measuring method comprising:
arranging a measuring device having:
a light source for irradiating excitation light;
an objective lens;
a first mirror;
a second mirror; and
a measuring device;
the second mirror being arranged between the objective lens and the first mirror with the mirror surface of the first mirror facing the mirror surface of the second mirror;
the first mirror having a curved surface with the center of curvature thereof disposed on the optical axis of the objective lens at the side of the second mirror;
the second mirror having an aperture at a position on the optical axis, the position of the aperture agreeing with the focal length of the objective lens; and
operating adjustment of the instrument when observing light generated in a sample of a wavelength different from the wavelength of excitation light by means of the measuring device and showing a level of luminance exceeding the measurable limit of the measuring device.

11. A measuring method comprising:
arranging a measuring device having:
a light source for irradiating light including rays of light having the wavelength of excitation light;
an objective lens for focusing light irradiated from the light source to a predetermined focusing position;
a first mirror for reflecting light from the objective lens;
a second mirror for reflecting light reflected by the first mirror, the second mirror having an aperture; and
a measuring device for measuring light generated from a sample and having a wavelength different from the wavelength of excitation light;
the sample being arranged between the first mirror and the second mirror;
the focusing position of the objective lens being made to agree with the position of the aperture;
the measuring device being adapted to measure light of a wavelength different from the wavelength of excitation light generated from the sample and passing through the aperture; and operating adjustment of the instrument when observing light generated in a sample of a wavelength different from the wavelength of excitation light by means of the measuring device and showing a level of luminance exceeding the measurable limit of the measuring device.

12. A measuring method comprising:
arranging a measuring device having:
a light source for irradiating light including rays of light having the wavelength of excitation light;
an objective lens for focusing light irradiated from the light source to a predetermined focusing position;
a first mirror for reflecting light from the objective lens;
a second mirror for reflecting light reflected by the first mirror, the second mirror having an aperture;
a focusing lens for focusing light generated from a sample and having a wavelength different from the wavelength of excitation light;
a measuring device for measuring light generated from a sample and having a wavelength different from the wavelength of excitation light; and
an excitation light cut filter arranged immediately in front of the measuring device at the light receiving side thereof to cut excitation light;
the sample being arranged between the first mirror and the second mirror;
the focusing position of the objective lens being made to agree with the position of the aperture so as to make the focusing position of excitation light and the measuring device show a conjugate positional relationship;
the measuring device being adapted to measure light of a wavelength different from the wavelength of excitation light generated from the sample; and
operating adjustment of the instrument when observing light generated in a sample of a wavelength different from the wavelength of excitation light by means of the measuring device and showing a level of luminance exceeding the measurable limit of the measuring device.

13. The method according to claim 10, wherein
the adjustment of the measuring device is arranging an ND filter on the measuring optical path, lowering the output of the light source if the output of the light source is variable, lowering the gain of the measuring device or reducing the exposure time of the measuring device.

14. A measuring method comprising:
arranging a first mirror;
arranging a microchip containing a sample on the first mirror;
arranging a second mirror for reflecting light reflected by the first mirror, the second mirror having an aperture;
causing excitation light from a light source for irradiating excitation light to be focused to the aperture by means of an objective lens and enter the microchip; and
measuring light radiated from the sample contained in the microchip and having a wavelength different from the wavelength of excitation light.

15. The measuring method according to claim 8, wherein $f<L$, where the air-equivalent length between the first mirror and the second mirror is L and the focal length of the first mirror is f.

16. The measuring method according to claim 8, wherein $f<L/2$, where the air-equivalent length between the first mirror and the second mirror is L and the focal length of the first mirror is f.

17. The measuring method according to claim 14, wherein the microchip is formed by:
a first substrate having a thickness of L1 and a refractive index of n1;
a second substrate having a thickness of L3 and a refractive index of n3; and
distance between the first substrate and the second substrate being L2, and a space containing a sample having a refractive index of n2, and
the distance between the first mirror and the second substrate being L4, the space being filled with a medium having a refractive index of n4, the focal length of the first mirror being f; and $L3/n3+L4/n4<Lf/(L-f)<L2/n2+L3/n3+L4/n4$;

the air-equivalent length L being defined to be $L=L1/n1+L2/n2+L3/n3+L4/n4$.

18. The measuring method according to claim 14, wherein the microchip is formed by:
a first substrate having a thickness of L1 and a refractive index of n1;
a second substrate having a thickness of L3 and a refractive index of n3; and
distance between the first substrate and the second substrate being L2, and a space containing a sample having a refractive index of n2, and
the distance between the first mirror and the second substrate being L4, the space being filled with a medium having a refractive index of n4, the focal length of the first mirror being f; and $L3/n3+L4/n4<L-(L^2-2fL)^{1/2}<L2/n2+L3/n3+L4/n4$;

the air-equivalent length L being defined to be $L=L1/n1+L2/n2+L3/n3+L4/n4$.

19. The measuring method according to claim 14, wherein $f<L$, where the air-equivalent length between the first mirror and the second mirror is. L and the focal length of the first mirror is f.

20. The measuring method according to claim 14, wherein $f<L/2$, where the air-equivalent length between the first mirror and the second mirror is L and the focal length of the first minor is f.

* * * * *